(12) United States Patent
Chen et al.

(10) Patent No.: US 11,501,433 B2
(45) Date of Patent: Nov. 15, 2022

(54) SYSTEMS AND METHODS FOR PROCESSING ELECTRONIC MEDICAL IMAGES TO DETERMINE ENHANCED ELECTRONIC MEDICAL IMAGES

(71) Applicant: Boston Scientific Scimed, Inc., Maple Grove, MN (US)

(72) Inventors: Longquan Chen, Andover, MA (US); Mussie Teshome Demisse, Chelsea, MA (US); Judith Fusman, West Orange, NJ (US); Aaron Silva, Somerville, MA (US); Andrea Cahill, Cambridge, MA (US); Evan Gyllenhaal, Sudbury, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 69 days.

(21) Appl. No.: 16/951,030

(22) Filed: Nov. 18, 2020

(65) Prior Publication Data

US 2021/0150706 A1 May 20, 2021

Related U.S. Application Data

(60) Provisional application No. 62/936,947, filed on Nov. 18, 2019.

(51) Int. Cl.
*G06T 7/00* (2017.01)
*G06T 7/62* (2017.01)
(Continued)

(52) U.S. Cl.
CPC .............. *G06T 7/0012* (2013.01); *G06T 7/13* (2017.01); *G06T 7/62* (2017.01); *G06T 7/70* (2017.01);
(Continued)

(58) Field of Classification Search
CPC ... G06T 7/0012; G06T 7/13; G06T 7/62; G06T 7/70; G06T 7/90; G06T 11/203;
(Continued)

(56) References Cited

U.S. PATENT DOCUMENTS

2004/0199077 A1* 10/2004 Hao ................... G06T 7/0012
600/443
2014/0142381 A1* 5/2014 Bae ................... A61B 1/00181
600/109

(Continued)

FOREIGN PATENT DOCUMENTS

CN 107730481 A 2/2018
CN 109190523 A 1/2019

OTHER PUBLICATIONS

International Search Report and Written Opinion dated Mar. 22, 2021 in International Application No. PCT/US2020/060944 (13 pages).

*Primary Examiner* — Siamak Harandi
(74) *Attorney, Agent, or Firm* — Bookoff McAndrews, PLLC.

(57) ABSTRACT

Systems and methods for processing electronic images from a medical device comprise receiving an image frame from the medical device, and determining a first color channel and a second color channel in the image frame. A location of an electromagnetic beam halo may be identified by comparing the first color channel and second color channel. Edges of an electromagnetic beam may be determined based on the electromagnetic beam halo, and size metrics of the electromagnetic beam may be determined based on the edges of the electromagnetic beam. A visual indicator on the image frame may be displayed based on the size metrics of the electromagnetic beam.

19 Claims, 5 Drawing Sheets

(51) Int. Cl.
*G06T 7/13* (2017.01)
*G06T 7/90* (2017.01)
*G06T 7/70* (2017.01)
*G06T 11/20* (2006.01)
*G06V 10/40* (2022.01)
*A61B 1/307* (2006.01)

(52) U.S. Cl.
CPC .............. *G06T 7/90* (2017.01); *G06T 11/203* (2013.01); *G06V 10/40* (2022.01); *A61B 1/307* (2013.01); *G06T 2207/10024* (2013.01); *G06T 2207/10068* (2013.01); *G06T 2207/30004* (2013.01); *G06V 2201/03* (2022.01)

(58) Field of Classification Search
CPC . G06T 2207/10024; G06T 2207/10068; G06T 2207/30004; G06T 2207/30084; G06V 10/40; G06V 2201/03; A61B 1/307
See application file for complete search history.

(56) References Cited

U.S. PATENT DOCUMENTS

2015/0320433 A1 11/2015 Navve et al.
2020/0106942 A1* 4/2020 Jiang ........................ G06T 5/50

* cited by examiner

SYSTEMS AND METHODS FOR PROCESSING ELECTRONIC MEDICAL IMAGES TO DETERMINE ENHANCED ELECTRONIC MEDICAL IMAGES

CROSS-REFERENCE TO RELATED APPLICATIONS

This application claims the benefit of priority from U.S. Provisional Application No. 62/936,947, filed on Nov. 18, 2019, which is incorporated by reference herein in its entirety.

TECHNICAL FIELD

Various aspects of the present disclosure relate generally to systems and methods useful in planning and/or performing medical procedures.

BACKGROUND

Substantial progress has been made towards increasing the effectiveness of medical treatment while reducing trauma and risks to the patient. Many procedures that once required open surgery now may be done with less invasive techniques, thus providing for less recovery time and risks of infection for the patient. Certain procedures requiring biopsy, electro-stimulation, tissue ablation, or removal of native or foreign bodies may be performed through minimally-invasive surgery.

In the field of urology, for example, renal calculi or kidney stones can accumulate in the urinary tract and become lodged in the kidney. Kidney stones are deposits of materials from the urine, typically minerals and acid salts. While smaller stones may pass from the body naturally, larger stones can require surgical intervention for removal. While open surgery was once the standard treatment for the removal of stones, other less invasive techniques, such as ureteroscopy and percutaneous nephrolithotomy/nephrolithotripsy (PCNL), have emerged as safer, effective alternatives. Additionally, advances in imaging technology have improved a medical professional's ability to identify and locate stones before and during procedures. Nevertheless, medical professionals still must analyze images to determine the location and size of stones and whether any stones are present. Moreover, the images are often obstructed, blurry, and/or otherwise difficult to evaluate, making the medical professional's task of discerning the presence or size of any stones challenging.

The systems, devices, and methods of the current disclosure may rectify some of the deficiencies described above, and/or address other aspects of the prior art.

SUMMARY

Examples of the present disclosure relate to, among other things, medical systems and methods. Each of the examples disclosed herein may include one or more of the features described in connection with any of the other disclosed examples.

In one example, the present disclosure includes a method for processing electronic images from a medical device comprising receiving an image frame from the medical device, and determining a first color channel and a second color channel in the image frame. A location of an electromagnetic beam halo may be identified by comparing the first color channel and second color channel. Edges of an electromagnetic beam may be determined based on the electromagnetic beam halo, and size metrics of the electromagnetic beam may be determined based on the edges of the electromagnetic beam. A visual indicator on the image frame may be displayed based on the size metrics of the electromagnetic beam.

In another example, the present disclosure includes a system for processing electronic images from a medical device, the system comprising at least one data storage device storing instructions for processing electronic images, and at least one processor configured to execute the instructions to perform operations for processing electronic images. The operations may comprise processing electronic images from a medical device comprising receiving an image frame from the medical device, and determining a first color channel and a second color channel in the image frame. A location of an electromagnetic beam halo may be identified by comparing the first color channel and second color channel. Edges of an electromagnetic beam may be determined based on the electromagnetic beam halo, and size metrics of the electromagnetic beam may be determined based on the edges of the electromagnetic beam. A visual indicator on the image frame may be displayed based on the size metrics of the electromagnetic beam.

In another example, the present disclosure includes a non-transitory computer-readable medium storing instructions that, when executed by a computer, cause the computer to perform operations for processing electronic images from a medical device. The operations may comprise processing electronic images from a medical device comprising receiving an image frame from the medical device, and determining a first color channel and a second color channel in the image frame. A location of an electromagnetic beam halo may be identified by comparing the first color channel and second color channel. Edges of an electromagnetic beam may be determined based on the electromagnetic beam halo, and size metrics of the electromagnetic beam may be determined based on the edges of the electromagnetic beam. A visual indicator on the image frame may be displayed based on the size metrics of the electromagnetic beam.

BRIEF DESCRIPTION OF THE FIGURES

The accompanying drawings, which are incorporated in and constitute a part of this specification, illustrate various exemplary embodiments and together with the description, serve to explain the principles of the disclosure.

DETAILED DESCRIPTION

Examples of the present disclosure include systems and methods to facilitate, and improve the efficiency and safety of minimally-invasive surgeries. For example, aspects of the present disclosure may provide a user (e.g., a physician, medical technician, or other medical service provider) with the ability to more easily identify, size, and, thus, remove kidney stones or other material from a patient's kidney or other organ. In some embodiments, for example, the present disclosure may be used in planning and/or performing a flexible ureteroscope procedure, with or without laser lithotripsy. Techniques discussed herein may also be applicable in other medical techniques, such as any medical technique utilizing an endoscope.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

Figure 1:
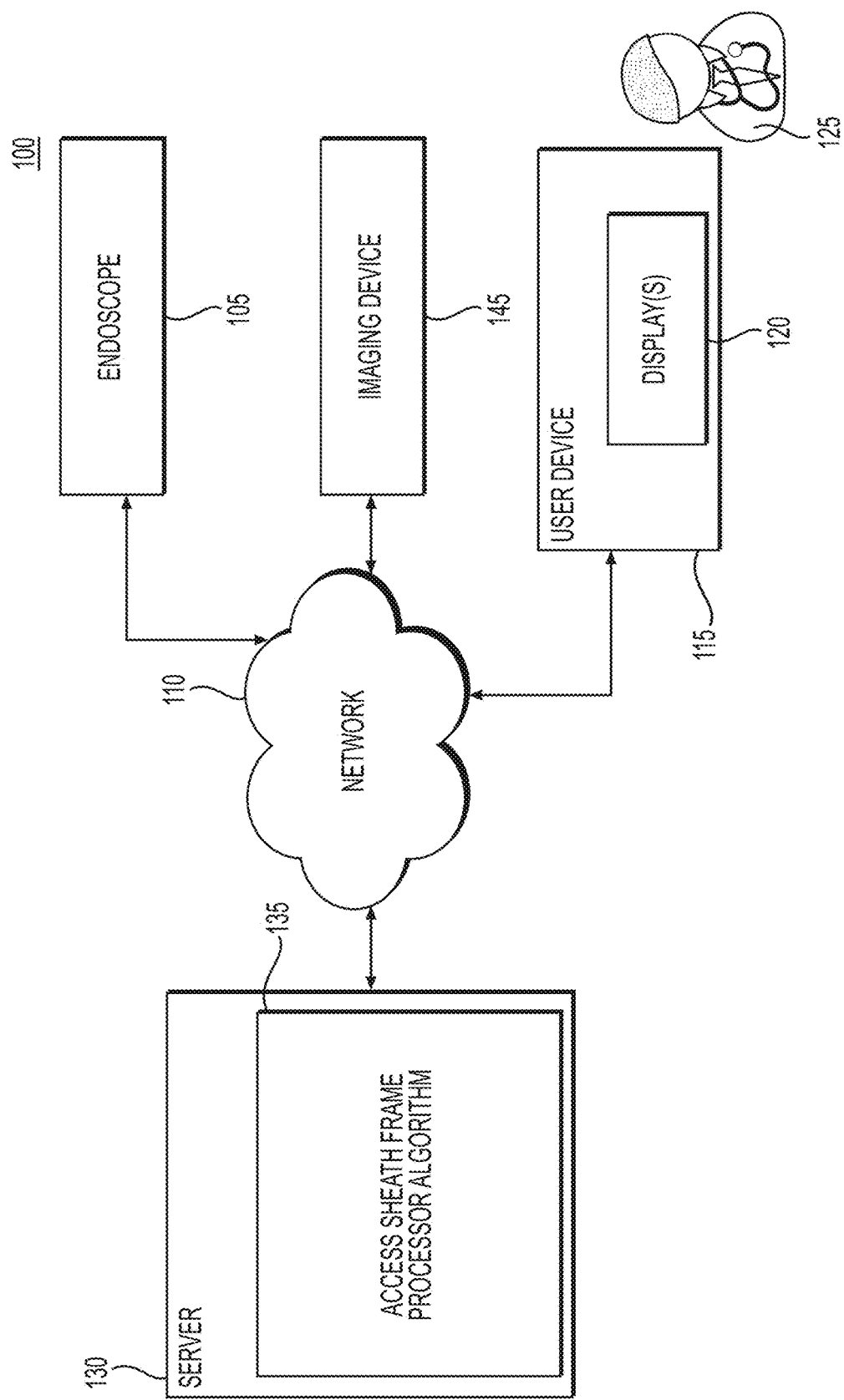
FIG. 1 illustrates a medical system, according to aspects of the present disclosure.

FIG. 1 illustrates a medical system 100 that includes a medical device such as an endoscope or other medical imaging device/medical device 105, a network 110, user device(s) 115 that may include display(s) 120 that may be viewed by a user/practitioner/physician/patient 125, and server(s) 130 that may comprise a frame processor 135 that may execute techniques discussed herein. The endoscope 105, user device(s) 115, and/or server 130 may be wire connected (as shown), wirelessly connected, or otherwise communicatively coupled. Alternatively, functionality of the server 130 may be performed on endoscope 105, user device 115, etc. The server 130, endoscope 105, and/or user device 115 may further comprise a single electronic device.

As shown in FIG. 1, endoscope 105 may be an insertion device such as, for example, a ureteroscope (e.g., Litho-Vue™ Digital Flexible Ureteroscope by Boston Scientific Corp.). With endoscope 105 positioned within a patient, for example, through the patient's urethra to a patient's kidney, a retrieval device (not shown) may be inserted to retrieve and remove material such as, for example, a kidney stone, with or without using laser lithotripsy. The endoscope 105 may record and/or transmit image and/or video data when inserted into a patient, and may have a light or other imaging source that may act to display images of the interior of a patient's vessels, organs, etc. A fiber optic cable or other light source may illuminate the interior of the patient. The endoscope 105 may be equipped with or receive a laser that may project at a lower power setting, such that it acts as an aiming beam. The aiming beam may act to inform the user of the endoscope where the laser is aiming, without illuminating at a high enough intensity to destroy tissue or the kidney stone. The laser may also, per signal from the user, emit electromagnetic waves at a higher intensity for performance of laser lithotripsy, which may be used to remove, break up, or otherwise destroy one or more organ obstructions, such as kidney stones.

Display 120 may be a single, or at least a dual display, with either multiple screens or multiple displays on one screen. In one example, one of the displays may show an image or images currently or previously obtained by endoscope 105. The other display may show an image or video obtained from one or more additional imaging devices 145, such as by X-ray, Magnetic Resonance Imaging, Computerized Tomography Scan, rotational angiography, ultrasound, or another appropriate internal imaging device. Alternatively, one of the displays 120 may show an image modified using one or more image enhancement techniques discussed herein, while another may display an unenhanced image. Alternatively, one of the displays 120 may show an image modified using one or more enhancement techniques discussed herein, while another of the displays 120 may show an image modified using one or more different enhancement techniques discussed herein.

The software or applications may manipulate, process, and interpret received images from imaging device 145 to identify the location, size, and characteristics of the aiming beam, kidney stone, or other material. As will be discussed further herein, the frame processor 135 may process and enhance received images from endoscope 105.

The physician may insert endoscope 105 into a patient when performing a medical procedure such as a lithotripsy to remove a kidney stone. The display 120 may become partially or completely obscured by pieces of kidney stone or other floating particulate matter, for example, when illuminated by a light on the endoscope 105. Pieces of the kidney stone may need to be removed via the exit channel used by the endoscope 105 (the access sheath, ureter, etc.). However, it may be difficult for the physician 125 to ascertain whether the kidney stone is too large to fit out the exit channel, and whether it should be broken up further in order to fit out the exit channel. The physician may attempt to remove the kidney stone in question via the exit channel, but the sharpness of the stone may cause tissue damage if it is too large, which may injure the patient, increase recovery time, etc. Techniques are needed to more effectively identify whether a kidney stone will fit out the exit channel.

Figure 2:
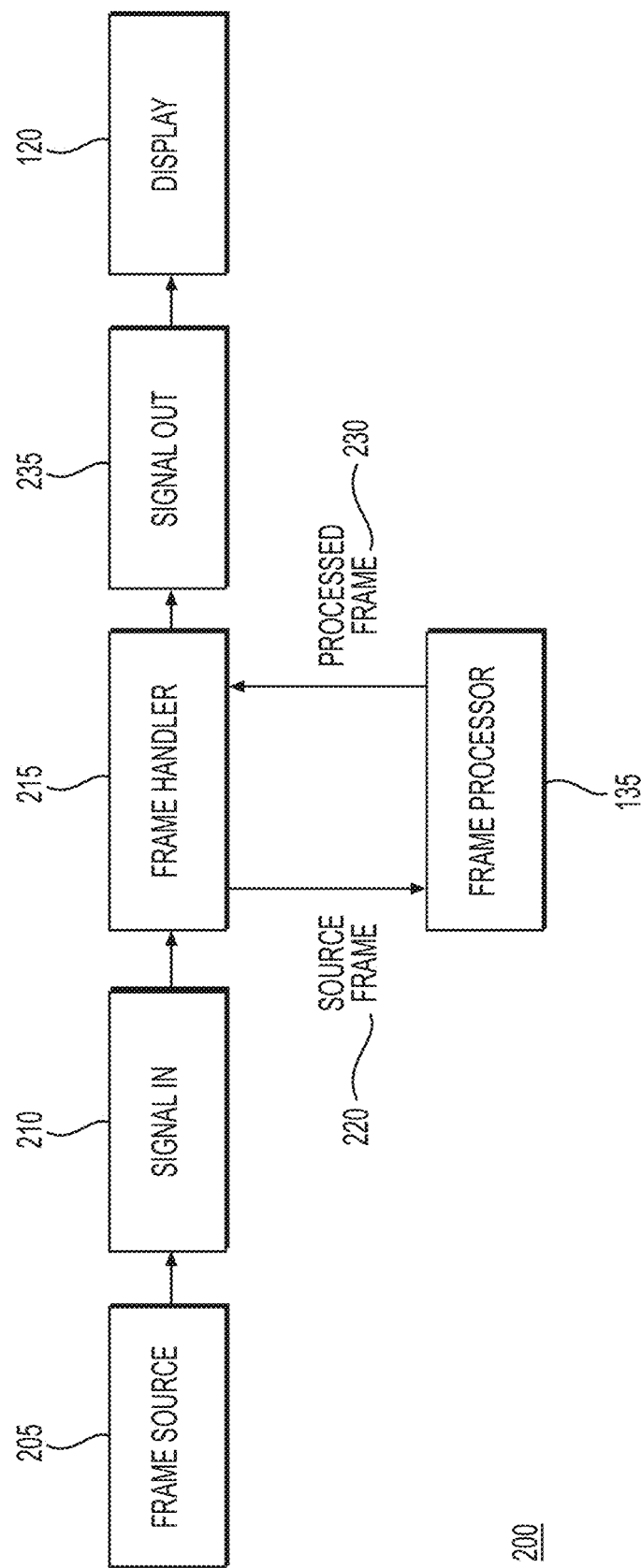
FIG. 2 is a flow diagram of an exemplary method for processing medical images, according to aspects of the present disclosure.

FIG. 2 is a flow diagram of an exemplary method for processing medical images, according to aspects of the present disclosure. A source of video or image frames 205, which may be any medical device, such as an endoscope 105 or imaging device 145, may provide frames to signal in 210. The frames may be provided to a frame handler 215, which may store a plurality of frames. One or more frames 220 may be provided to a frame processor 135, which may produce one or more processed frames 230 via techniques discussed herein. The processed frames 230 may be provided to the signal out 235, which may be shown on display 120.

The signal in 210 may be a software handler that may transmit that a new frame has been received. The frame handler 215 may either directly send a frame via the signal out 235 to a display 120, or it may send one or more frames to the frame processor 135. As will be discussed elsewhere herein, the frame processor 135 may perform object size determination techniques. The frame handler 215 may also send the original frame to the display 120, and also send a copy of the frame to the frame processor 135. The processed frame 230 may be received and also forwarded to the display 120. This may allow for the original frame to be displayed alongside the processed frame 230 at the display 120. Alternatively, the frame handler 215 may send the source frame 220 to the frame processor 135, and the frame processor may return a processed frame 230 that comprises a dual display of the original and enhanced frame. Accordingly, the processed frame 230 may be larger than the source frame. The frame processor 135 may further add buttons or other user interface elements to the processed frame 230.

Although techniques discussed herein are discussed as happening on the frame processor 135, which may be depicted as being located on a single device, any of the functions of the frame processor may be spread across any number of devices, for example, any of the devices depicted in system 100. Further, one or more of the signal in 210, frame handler 215, and/or signal out 235 may be housed on one or more servers 130, or any of the other devices pictured on system 100.

Figure 3:
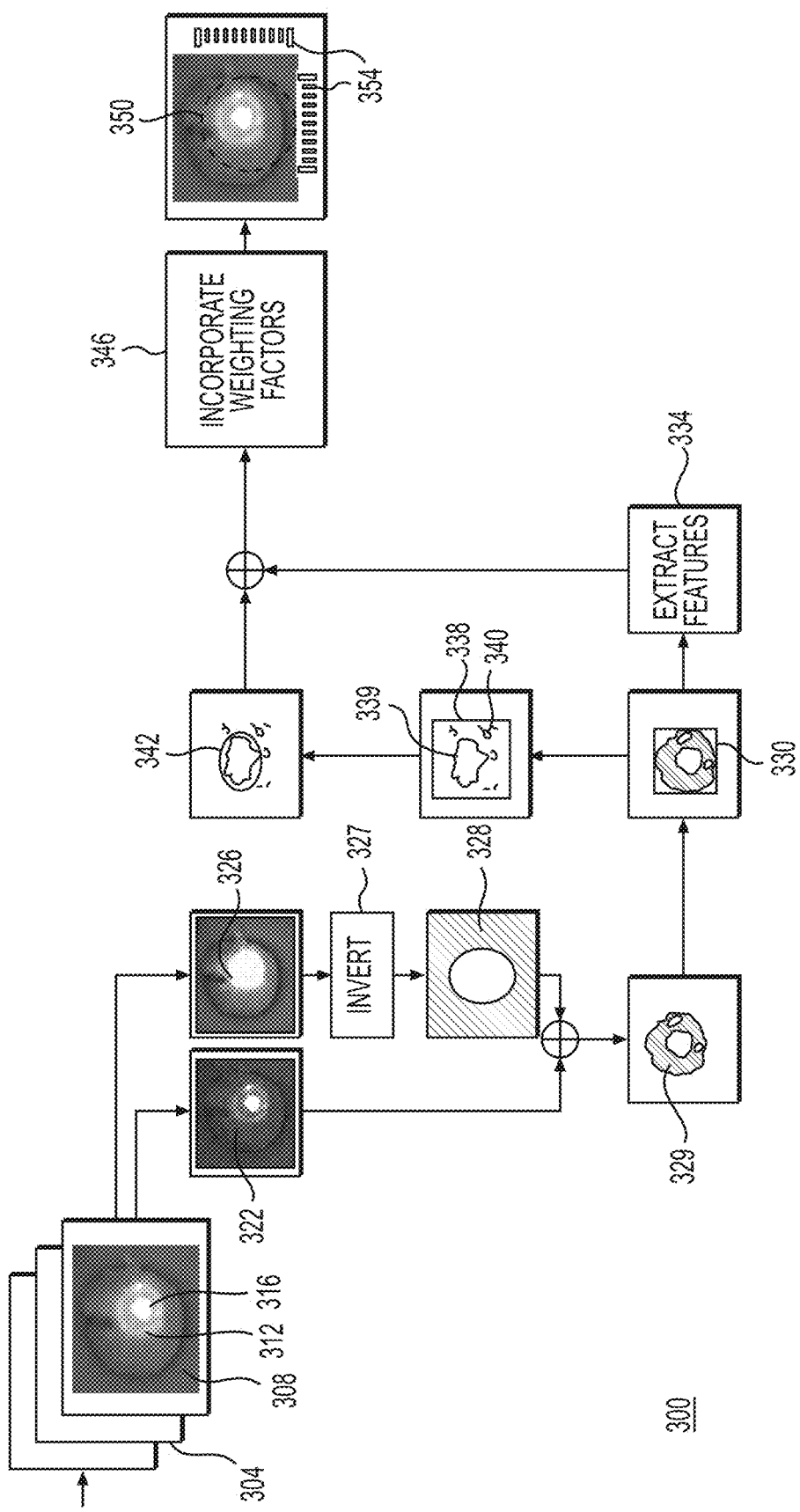
FIG. 3 is a flow diagram of an exemplary method for determining a size of an object in medical images, according to aspects of the present disclosure.

FIG. 3 is a flow diagram of an exemplary method for processing medical images to determine the size of objects, according to aspects of the present disclosure. A plurality of frames 304 may be received from a frame source. The frame source may comprise an endoscope 105 or other medical imaging device 145. One or more frames 304 may be accumulated at a frame buffer. A frame may comprise an image of a kidney stone 308, or other object. While the kidney stone 308 may be illuminated by a light source on the tip of the endoscope or other medical device 105, such as by an optical fiber emitting white light, a laser beam 316, or other electromagnetic beam, may also be present and allow for aiming the tip of the endoscope, either for purposes of retrieving the kidney stone or performing lithotripsy, etc. The beam 316, when illuminated, may cause a halo 312 to be visible around the beam, which may be due to the intensity of the laser. Steps may then be taken to determine the size of the beam 316.

The halo 312 may be distinguished from the beam 316. As lasers are typically a particular color, such as red, in the blue or green "non-matching" channels 322 there may be no trace or faint trace of the beam 316, and no trace of the halo 312. Conversely, in the "matching" red channel 326, the laser and the halo 312 might appear together as a large, bright, and indistinguishable entity. Similarly, a green laser and its halo might show up as a single bright indistinguishable entity in the green color channel, while at least the lower-intensity halo would not show up in the red channel or blue channel, etc. Thus, the color of the laser may be initially determined for purposes of separating color channels and performing techniques discussed herein. In addition, the endoscope may have a white light from an optical cable to help the user navigate. The white light may create reflections that might be confused by the algorithm as the aiming beam. By finding the aiming beam by comparing different color channels, this problem is avoided. A white light would show up equally in different color channels. A colored laser, or at least the halo, may show up primarily in the corresponding color channel.

The aiming beam may be intense in all color channels, even though the aiming beam may be a laser of a particular color. This may make distinguishing the aiming beam from other light reflections, for example a light reflection from an LED on the endoscope, difficult. However, the aiming beam may have an associated halo around it, which may allow for differentiation of the aiming beam from other light sources or reflections. In addition, the halo may only appear in a particular color channel, for example the channel of the color of the laser. Thus, the halo may be reliably identified by comparing different color channels. Once the beam of matching channel 326 (e.g. red channel for a red laser) and smaller beam 322 of the non-matching channel (green and/or blue channels for a red laser) 322 are determined, the two channels may be combined to form a mask area in order to more accurately determine the halo. This may be done by subtracting the non-matching channel 322 from the matching channel 326, which may produce an image of the halo with the beam 316 removed at 329. Alternatively, one of the channels may be inverted at 327 to form an inverted channel 328. The inverted channel 328 may be added to the, e.g., non-matching channel to form the halo 329. A bounding box or other boundary may be placed around the halo/mask area 330 for further image analysis.

After the bounding box 330 is determined, the aiming beam 339 in the center of the halo and within the bounding box may be determined. Image artifacts 340 may also be present. The artifacts 340 may show up, for example, if the laser reflects off of objects near the aiming beam itself. The algorithm, by comparing the various candidate aiming beams, may consider the largest object to be the true aiming beam 339, and may discard or disregard the artifacts 340. The edges of the true aiming beam 339 may be determined using an algorithm such as Canny edge detection, Hough transform, etc. The algorithm may then approximate the true shape and size of the aiming beam 339 by placing a circle or ellipse around the aiming beam to form an aiming beam ellipse 342. This may be done dynamically, or the shape of the aiming beam may be previously known. This ellipse placement may be performed based on the determined aiming beam edges. Multiple candidate ellipses may be fit over the detected edges, and the best-fitting ellipse may be determined, e.g. the aiming beam ellipse 342. Metrics may be determined for the aiming beam ellipse 342, such as the measurements of the major and minor axes.

The aiming beam may be of a standard, predetermined size and shape. Since the aiming beam 316 is a laser or other highly directional or unidirectional electromagnetic light source, it does not get substantially larger with distance. Hence, whatever object upon which the aiming beam is projected may be measured by using the aiming beam and/or its halo as a standard metric. Thus, kidney stones or other objects may be measured by evaluating the aiming beam and/or halo. However, difficulties may arise that may complicate an accurate measurement. Kidney stones are often jagged and contain crevices or other irregularities that distort the apparent shape of the aiming beam. Thus, the aiming beam may appear abnormally small or abnormally large, which may cause incorrect estimates of the size of any object being measured based on the aiming beam.

To mitigate this problem, the image of surface upon which the aiming beam is being aimed may be evaluated by image analysis within the bounding box, or otherwise within a predetermined distance of the aiming beam 316 and/or halo 312, may be extracted at 334. The image features may comprise image lighting, texture, entropy, artifact detection, etc. The extracted image features plus the major and minor axes of the ellipse 342 may be provided to a trained machine-learning system, which may apply weights to alter the estimated size of the aiming beam 316 and/or halo 312.

The machine learning system may be trained. A size (e.g., in pixels) of a ground truth indicator may be determined. The ground truth indicator may be a physically drawn circle or other shape onto an image of the kidney stone representing the true size of aiming beam. In the training process, the size of the physically drawn circle will be extracted from the image. A correlation between the size of the ground truth indicator and the aiming beam properties (major and minor axes of ellipse 342, image lighting, texture, entropy, artifact detection, etc.) may be determined. In the inference step of the production version, the machine learning model may calculate the size of the aiming beam. This may be accurately performed despite distortions produced by the surface upon which the aiming beam is being projected.

As discussed above, the dimensions of the aiming beam may be known. For example, the aiming beam may be a laser that, when shined on a surface, creates a "dot" 5 mm across. As the laser is a directional beam, the dot may be 5 mm across no matter how far away the object is upon which the dot is being shined. Thus, based on the final estimated shape and/or size of the aiming beam, measurements of the surface on which the aiming beam is projected may be determined. This may be done by assessing the size of an object relative to the known size of the laser dot. For example, if a laser dot is known to be 5 mm across, and the kidney stone upon which it is shined is approximately double the width of the laser dot, the kidney stone may be determined to be 10 mm across.

Using this same technique, the size of the exit channel may be determined and displayed to the user 125. Thus, using this scaling technique, the size of objects may be determined, and the accurate size of projected virtual objects may also be determined. A visual indicator 350 representing the size of the exit channel relative to the surface upon which the aiming beam is projected may be displayed on the display. The user 125 may thus be able to determine if the kidney stone or other object, upon which the aiming beam is shined, will fit out the exit channel visually and with minimal cognitive load. Alternatively or in addition, one or more rulers may be displayed, such as rulers 354 along the X or Y axis. Visual indicators of the bounding box 330 and/or final aiming beam ellipse 342 may also be displayed on a display to the user 125.

Figure 4:
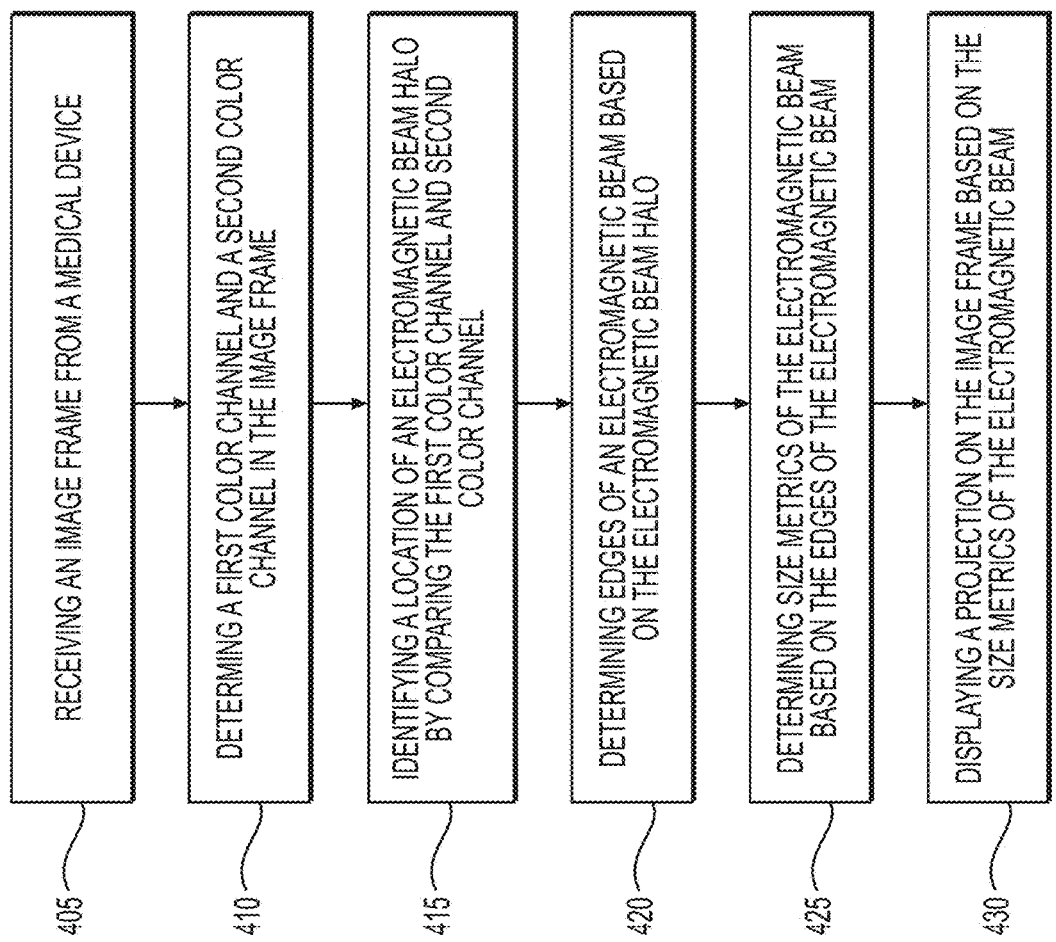
FIG. 4 is a flow diagram of an exemplary method for medical image enhancement, according to aspects of the present disclosure.

FIG. 4 is a flow diagram of an exemplary method for determining medical image enhancement, according to techniques discussed herein. At step 405, an image frame from the medical device may be received, and at step 410 a first color channel and a second color channel in the image frame may be determined. At step 415 a location of an electromagnetic beam halo may be identified by comparing the first color channel and second color channel. At step 420, edges of an electromagnetic beam may be determined based on the electromagnetic beam halo, and at step 425 size metrics of the electromagnetic beam may be determined based on the edges of the electromagnetic beam. At step 430 a visual indicator or other projection on the image frame may be displayed based on the size metrics of the electromagnetic beam. As discussed elsewhere herein, the visual indicator may comprise a visual representation of the exit channel, a ruler, a bounding box, an electromagnetic beam halo, and/or an electromagnetic beam.

Figure 5:
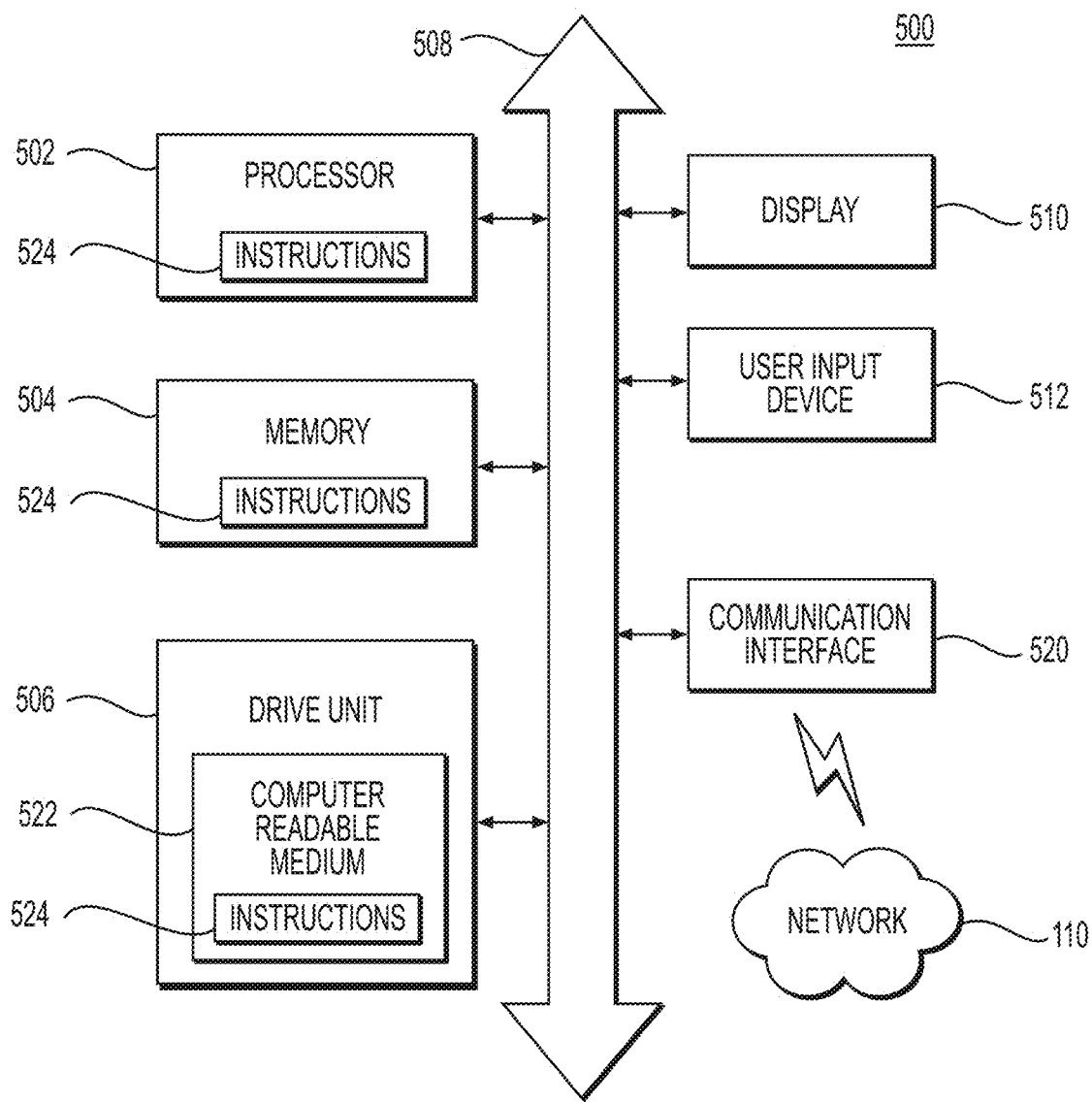
FIG. 5 illustrates an exemplary system that may be used in accordance with techniques discussed in FIGS. 1-4, according to aspects of the present disclosure.

FIG. 5 illustrates an exemplary system that may be used in accordance with techniques discussed in FIGS. 1-4, according to aspects of the present disclosure. FIG. 5 is a simplified functional block diagram of a computer that may be configured as server 130, endoscope 105, imaging device 145, and/or user device 115, according to exemplary embodiments of the present disclosure. Specifically, in one embodiment, any of the user devices, servers, etc., discussed herein may be an assembly of hardware 500 including, for example, a data communication interface 520 for packet data communication. The platform also may include a central processing unit ("CPU") 502, in the form of one or more processors, for executing program instructions. The platform may include an internal communication bus 508, and a storage unit 506 (such as ROM, HDD, SDD, etc.) that may store data on a computer readable medium 522, although the system 500 may receive programming and data via network communications. The system 500 may also have a memory 504 (such as RAM) storing instructions 524 for executing techniques presented herein, although the instructions 524 may be stored temporarily or permanently within other modules of system 500 (e.g., processor 502 and/or computer readable medium 522). The system 500 also may include input and output ports 512 and/or a display 510 to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

The disclosed techniques may help enable efficient and effective procedures to breakup and/or remove material from a patient's organ. In particular, the user may easily view the processed frames to assist with, for example, removing kidney stones within the patient's kidney Moreover, while examples discussed in this disclosure are commonly directed to ureteroscopic kidney stone removal, with or without lithotripsy, it is further contemplated that the systems and procedures discussed herein may be equally applicable to other material removal procedures. For example, the systems and methods discussed above may be used during a percutaneous nephrolithotomy/nephrolithotripsy (PCNL) to plan for a procedure and mid-procedure to locate any missed kidney stones. The systems and methods discussed above may also be used to plan for or conduct procedures to remove ureteral stones, gallstones, bile duct stones, etc.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A system for processing electronic images from a medical device, comprising:
   at least one data storage device storing instructions for processing electronic images; and
   at least one processor configured to execute the instructions to perform operations for processing electronic images, the operations comprising:
   receiving an image frame from the medical device;
   determining a first color channel and a second color channel in the image frame;
   identifying a location of an electromagnetic beam halo by comparing the first color channel and second color channel;
   determining edges of an electromagnetic beam based on the electromagnetic beam halo;
   determining size metrics of the electromagnetic beam based on the edges of the electromagnetic beam; and
   displaying a visual indicator on the image frame based on the size metrics of the electromagnetic beam.

2. The system of claim 1, the operations further comprising:

extracting features from the image frame within a predetermined distance of the electromagnetic beam and/or electromagnetic beam halo; and determining a size of the visual indicator on the image frame based on the extracted features.

3. The system of claim 2, wherein the size of the visual indicator on the image is determined based on a weighting of each of the extracted features.

4. The system of claim 1, wherein the visual indicator on the image frame corresponds to a size of an exit channel through which objects are passed.

5. The system of claim 1, wherein comparing the first color channel and the second color channel further comprises:

determining that the first color channel depicts the electromagnetic beam and the electromagnetic beam halo;

determining that the second color channel depicts the electromagnetic beam; and subtracting, or adding the inverse of, the second color channel and the first color channel to identify the location of an electromagnetic beam halo.

6. The system of claim 1, wherein determining the edges of the electromagnetic beam comprises:

determining an approximated electromagnetic beam based on the electromagnetic beam halo;

distinguishing the approximated electromagnetic beam from image artifacts based on the size of the approximated electromagnetic beam relative to the image artifacts; and fitting a circle or an ellipse to the approximated electromagnetic beam.

7. The system of claim 1, wherein the first color channel is determined so as to match a predetermined color of the electromagnetic beam, and wherein the second color channel is determined so as to not match the predetermined color of the electromagnetic beam.

8. The system of claim 1, wherein the electromagnetic beam is a laser.

9. The system of claim 1, wherein the size metrics correspond to a diameter or radius of the electromagnetic beam.

10. A method for processing electronic images from a medical device, comprising:

receiving an image frame from the medical device;

determining a first color channel and a second color channel in the image frame;

identifying a location of an electromagnetic beam halo by comparing the first color channel and second color channel;

determining edges of an electromagnetic beam based on the electromagnetic beam halo;

determining size metrics of the electromagnetic beam based on the edges of the electromagnetic beam; and displaying a visual indicator on the image frame based on the size metrics of the electromagnetic beam.

11. The method of claim 10, further comprising:

extracting features from the image frame within a predetermined distance of the electromagnetic beam and/or electromagnetic beam halo; and determining a size of the visual indicator on the image frame based on the extracted features.

12. The method of claim 11, wherein the size of the visual indicator on the image is determined based on a weighting of each of the extracted features.

13. The method of claim 10, wherein the visual indicator on the image frame corresponds to a size of an exit channel through which objects are passed.

14. The method of claim 10, wherein comparing the first color channel and the second color channel further comprises:

determining that the first color channel depicts the electromagnetic beam and the electromagnetic beam halo;

determining that the second color channel depicts the electromagnetic beam; and subtracting, or adding the inverse of, the second color channel and the first color channel to identify the location of an electromagnetic beam halo.

15. The method of claim 10, wherein determining the edges of the electromagnetic beam comprises:

determining an approximated electromagnetic beam based on the electromagnetic beam halo;

distinguishing the approximated electromagnetic beam from image artifacts based on the size of the approximated electromagnetic beam relative to the image artifacts; and fitting a circle or an ellipse to the approximated electromagnetic beam.

16. The method of claim 10, wherein the first color channel is determined so as to match a predetermined color of the electromagnetic beam, and wherein the second color channel is determined so as to not match the predetermined color of the electromagnetic beam.

17. The method of claim 10, wherein the electromagnetic beam is a laser.

18. The method of claim 10, wherein the size metrics correspond to a diameter or radius of the electromagnetic beam.

19. A non-transitory computer-readable medium storing instructions that, when executed by a computer, cause the computer to perform operations for processing electronic images from a medical device, the operations including:

receiving an image frame from the medical device;

identifying a location of an electromagnetic beam shined upon a surface in the image frame;

analyzing the electromagnetic beam to determine size metrics of the surface upon which the electromagnetic beam is shined; and displaying a visual indicator on the image frame based on the size metrics of the electromagnetic beam, wherein analyzing the electromagnetic beam to determine size metrics further comprises:

determining a first color channel and a second color channel in the image frame;

identifying a location of an electromagnetic beam halo by comparing the first color channel and second color channel;

determining edges of an electromagnetic beam based on the electromagnetic beam halo; and determining size metrics of the electromagnetic beam based on the edges of the electromagnetic beam.

* * * * *